(12) United States Patent
Sarvazyan et al.

(10) Patent No.: US 6,569,108 B2
(45) Date of Patent: May 27, 2003

(54) REAL TIME MECHANICAL IMAGING OF THE PROSTATE

(75) Inventors: Armen P. Sarvazyan, Lambertville, NJ (US); Vladimir Egorov, Plainsboro, NJ (US)

(73) Assignee: Profile, LLC, Birmingham, AL (US)

( * ) Notice: Subject to any disclaimer, the term of this patent is extended or adjusted under 35 U.S.C. 154(b) by 13 days.

(21) Appl. No.: 09/819,419

(22) Filed: Mar. 28, 2001

(65) Prior Publication Data
US 2002/0143275 A1 Oct. 3, 2002

(51) Int. Cl.$^7$ .......................... A61B 5/103; A61B 5/117
(52) U.S. Cl. ....................................................... 600/587
(58) Field of Search ............................. 600/587, 439, 600/561, 461, 595; 73/787, 818

(56) References Cited

U.S. PATENT DOCUMENTS

| | | |
|---|---|---|
| 4,250,894 A | 2/1981 | Frei et al. |
| 4,423,738 A | 1/1984 | Newgard |
| 4,580,574 A | 4/1986 | Gavish |
| 4,711,248 A | 12/1987 | Steuer et al. |
| 4,722,348 A | 2/1988 | Ligtenberg et al. |
| 4,799,491 A | 1/1989 | Eckerle |
| 4,802,488 A | 2/1989 | Eckerle |
| 4,809,710 A | 3/1989 | Williamson |
| 4,860,761 A | 8/1989 | Yamasawa et al. |
| 4,869,265 A | 9/1989 | McEwen |
| 4,893,634 A | 1/1990 | Kulik et al. |
| 4,947,851 A | 8/1990 | Sarvazyan et al. |
| 5,067,491 A | 11/1991 | Taylor, II et al. |
| 5,078,142 A | 1/1992 | Siczek et al. |
| 5,099,848 A | 3/1992 | Parker et al. |
| 5,107,837 A | 4/1992 | Ophir et al. |
| 5,115,808 A | 5/1992 | Popovic et al. |
| 5,170,790 A | 12/1992 | Lacoste et al. |
| 5,178,148 A | 1/1993 | Lacoste et al. |

(List continued on next page.)

FOREIGN PATENT DOCUMENTS

| | | |
|---|---|---|
| WO | WO 94/14375 | 7/1994 |
| WO | WO 95/02992 | 2/1995 |

OTHER PUBLICATIONS

Littrup et al., "The Benefit and Cost of Prostate Cancer Early Detection," CA Cancer Journ. for Clinicians, vol. 43, pp. 134–149 (1993).

Smith et al., "Interexaminer Variability of Digital Rectal Examination in Detecting Prostate Cancer," Urology, vol. 45, pp. 70–74 (1995).

(List continued on next page.)

*Primary Examiner*—Max F. Hindenburg
*Assistant Examiner*—Brian Szmal
(74) *Attorney, Agent, or Firm*—Mathews, Collins, Shepherd & McKay, P.A.

(57) ABSTRACT

The present invention relates to a method for real time mechanically imaging the prostate with a transrectal probe. In the method, the prostate image is synthesized and displayed in real time during the examination process. In a preferred embodiment, a compact prostate examination device comprises a probe sized to fit within the rectum and having a head with a tactile sensor longer than the axial length of an average prostate, an electronic unit and a display. As the pressure sensing part of the head is pressed against and moved over the prostate, it generates signals characterizing mechanical structure of the examined area. An accelerometer based motion tracking system is mounted in the probe for determining the position of the pressure transducer array during prostate examination. The electronic unit incorporated into the handle of the probe receives the pressure and motion data to calculate mechanical and geometrical features of the prostate and displays it on the display.

33 Claims, 11 Drawing Sheets

U.S. PATENT DOCUMENTS

| | | | |
|---|---|---|---|
| 5,247,937 A | | 9/1993 | Ophir et al. |
| 5,265,612 A | | 11/1993 | Sarvazyan et al. |
| 5,278,776 A | | 1/1994 | Fisher et al. |
| 5,293,870 A | | 3/1994 | Ophir et al. |
| 5,402,793 A | | 4/1995 | Gruner et al. |
| 5,423,332 A | | 6/1995 | Zirps et al. |
| 5,474,070 A | | 12/1995 | Ophir et al. |
| 5,522,399 A | | 6/1996 | Wilk et al. |
| 5,524,636 A | * | 6/1996 | Sarvazyan et al. .......... 600/587 |
| 5,526,820 A | | 6/1996 | Khoury |
| 5,785,663 A | * | 7/1998 | Sarvazyan ................. 600/561 |
| 5,836,894 A | * | 11/1998 | Sarvazyan ................. 600/561 |
| 5,922,018 A | * | 7/1999 | Sarvazyan ................. 600/587 |
| 5,989,199 A | * | 11/1999 | Cundari et al. ............ 600/587 |
| 6,063,031 A | * | 5/2000 | Cundari et al. ............ 600/439 |
| 6,142,959 A | | 11/2000 | Sarvayzan et al. |

OTHER PUBLICATIONS

Learner et al., "Sono Elasticity: Medical Elasticity Images Derived from Ultrasound Signals in Mechanically Vibrated Targets," Acoustical Imaging, vol. 16, 317 (1988).

T.A. Krouskop et al., "A Pulsed Doppler Ultrasonic System for Making Non–Invasive Measurement of Mechanical Properties of Soft Tissue," 24 J. Rehab. Res. Dev., vol. 24, 1 (1987).

Y. Yamakoshi et al., "Ultrasonic Imaging of Internal Vibration of Soft Tissue Under Forced Vibration," IEEE Transactions on Ultrasonics Ferroelectrics and Frequency Control, vol. 7, No. 2, p. 45 (1990).

R. Rubens et al., "Sonoelasticity Imaging of Prostate Cancer: In Vitro Results," Journal of Radiology, 195, No. 2, May 1995, pp. 379–383.

Sarvazyan et al., "Biophysical Bases of Elasticity Imaging," Acoustical Imaging, vol. 21, pp. 223–240 (1995).

Sarvazyan et al., "A New Philosophy of Medical Imaging," Medical Hypotheses, vol. 36, pp. 327–335 (1991).

* cited by examiner

REAL TIME MECHANICAL IMAGING OF THE PROSTATE

This invention was made with government support under SBIR Grants No. 1R43 CA82620-01A1 awarded by the National Institutes of Health, National Cancer Institute. The government has certain rights in this invention.

BACKGROUND OF THE INVENTION

1. Field of the Invention

The present invention relates to a method and device for mechanically imaging the prostate. It is also applicable to mechanical imaging of tissues and glands, including but not limited to, through natural openings in a human being, i.e. mouth, ear(s), rectum, etc. channels. It is also applicable to determination of relative stiffness or elasticity of tissues or glands, i.e. breast. In all cases both human beings and animals, both alive and dead, can be a subject for mechanically imaging.

2. Description of Related Art

Conventional methods for early detection of prostate cancer include digital rectal examination (DRE). Digital rectal examination or palpation, that is an examination using the sense of touch, is based on the significant differences in elasticity of normal tissues and certain lesions. Palpation has been a commonly used test by general practitioners and specialists and is recommended as a part of an annual general preventive physical examination for all men 40 years of age and older. The effectiveness and reliability of palpation is dependent on the level of skill of the examiner, since the finger as an instrument does not provide any quantitative information, and therefore the examiner must instinctively relate what he/she senses by the finger to their previous experience with palpation, as described in Littrup et al., *The Benefit and Cost of Prostate Cancer Early Detection*, CA Cancer Journ. for Clinicians, Vol. 43, pp. 134–149 (1993). It has been found that the disagreement between the palpatory findings of experienced urologists is about 20%, as described in Smith et al., *Interexaminer Variability of Digital Rectal Examination in Detecting Prostate Cancer*, Urology, Vol. 45, pp. 70–74 (1995). The disagreement within inexperienced examiners, who are most likely to carry the bulk of cancer screening, is much higher. Once a lesion is palpated, documentation of the abnormality depends on the precision of a physician's description or a freehand diagram.

Several authors have proposed various types of devices mimicking palpation to detect tumors using different types of pressure sensors. For example, U.S. Pat. No. 4,250,894, describes an instrument for breast examination that uses a plurality of spaced piezoelectric strips which are pressed into the body being examined by a pressure member which applies a given periodic or steady stress to the tissue beneath the strips.

Another approach to evaluate the elasticity of the tissues uses indirect means, such as conventional imaging modalities (ultrasound or MRI) which are capable of detecting motion of a tissue subjected to an external force. One approach attempts to determine the relative stiffness or elasticity of tissue by applying ultrasound-imaging techniques while vibrating the tissue at low frequencies. See, e.g., J. J. Parker et al., U.S. Pat. No. 5,099,848; R. M. Learner et al., *Sono-Elasticity: Medical Elasticity Images Derived From Ultrasound Signals in Mechanically Vibrated Targets*, Acoustical Imaging, Vol. 16, 317 (1988); T. A. Krouskop et al., *A Pulsed Doppler Ultrasonic System for Making Non-Invasive Measurement of Mechanical Properties of Soft Tissue*, 24 J. Rehab. Res. Dev. Vol. 24, 1 (1987); Y. Yamakoshi et al., *Ultrasonic Imaging of Internal Vibration of Soft Tissue Under Forced Vibration*, IEEE Transactions on Ultrasonics Ferroelectrics, and Frequency Control, Vol. 7, No. 2, Page 45 (1990).

U.S. Pat. Nos. 6,142,959; 5,922,018 and 5,836,894 to Sarvazyan et al., describe devices for mechanical imaging of the prostate using a transrectal probe. The prostate imaging is achieved by evaluating the spatial changes of stress pattern over the prostate compressed by the probe. The devices enable physicians to quantitatively and objectively characterize geometrical and mechanical features of the prostate. However, the physician doesn't have a feedback in real time, while prostate examination, which decreases the data collection efficacy.

It is desirable to provide an improved real time method and device for palpation and mechanical imaging of the prostate.

SUMMARY OF THE INVENTION

The present invention relates to a method for real time mechanically imaging the prostate with a transrectal probe. The present invention provides a means for electronic palpation of the prostate, objective and quantitative assessment of the prostate conditions using tactile sensors. In the method, the prostate image is synthesized and displayed in real time during the examination process. In a preferred embodiment, the compact prostate examination device comprises a probe sized to fit within the rectum and having a head with a tactile sensor longer than the axial length of an average prostate, an electronic unit and a display. As the pressure sensing part of the head is pressed against and moved over the prostate, it generates signals characterizing mechanical structure of the examined area. An accelerometer-based motion tracking system is mounted in the probe for determining the position of the pressure transducer array during prostate examination. The electronic unit incorporated into the handle of the probe receives the pressure and motion data to calculate mechanical and geometrical features of the prostate and displays it on the display.

Preferably, the tactile sensor includes a plurality of accelerometers to be used as a motion tracking system for determination of probe coordinates relative to the examined prostate. In an alternate preferred embodiment of the present invention the tactile sensor comprises a magnetometer-based motion tracking system. Thereafter, the pressure response is used in real time to generate mechanical imaging results. Alternatively, the method and device can be used for real time mechanically imaging any gland or tissue.

The invention will be more fully described by reference to the following drawings.

DETAILED DESCRIPTION

Figure 1:
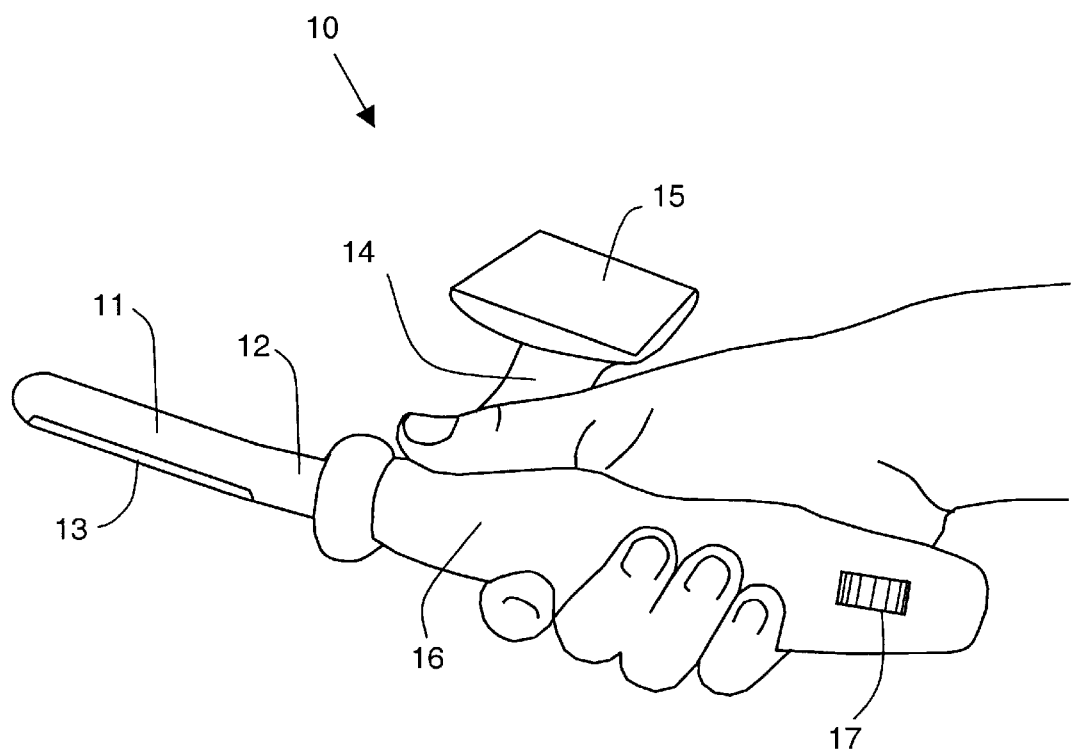
FIG. 1 is a perspective view of an embodiment of the probe of the present invention including a tactile sensor and electronic unit with a two-dimensional display attached to the probe handle.

Reference will now be made in greater detail to a preferred embodiment of the invention, an example of which is illustrated in the accompanying drawings. Wherever possible, the same reference numerals will be used throughout the drawings and the description to refer to the same or like parts.

The method for transrectal imaging of the prostate is based on the technology of medical imaging described in U.S. Pat. Nos. 6,142,959; 5,922,018 and 5,836,894, which are incorporated herein by reference. This method is referred to herein as mechanical imaging (MI). The essence of MI is the reconstruction of the internal structure of soft body tissues by measuring a surface stress pattern using a pressure sensing assembly. The pattern of mechanical stress and its changes as a function of applied pressure and time contain comprehensive information on the mechanical properties and geometry of the internal structures of the body tissues.

FIG. 1 is a perspective view of a preferred embodiment of a prostate probe 10 sized to fit within the rectum. Probe 10 comprises tactile sensor 13 mounted on head 11. Tactile sensor 13 generates signals in response to forces imposed on tactile sensor 13 as it is pressed against and moved over the prostate. Probe 10 further comprises shaft 12 coupled to handle 16. Control wheel 17 is formed in handle 16. Two-dimensional display 15 is attached to handle 16 with display support 14. Alternatively, the display can be built into the probe handle. The display or more than one display can be connected with or attached to, or mounted or laid onto a support or more than one support. An electronic unit (not shown FIG. 1) is incorporated inside the handle 16.

During prostate examination, in accordance with the present invention, probe 10 is inserted into the rectum and manipulated within the rectum using handle 16. In essence, head 11 is moved within the rectum and is pressed against the prostate. The electronic unit receives electrical signals generated by tactile sensor 13 in response to forces imposed on tactile sensor 13 and calculates in real time a pressure profile which characterizes prostate cross-section. The pressure profile is visualized on display 15. In a first phase of the prostate examination depth of insertion of probe 13 is adjusted so that the prostate is located close to the center of tactile sensor 13. In a second phase of prostate examination the prostate is palpated in accordance with a predetermined trajectory to collect pressure response and motion data of probe 10 for calculating mechanical imaging of the prostate and its inner structure.

In the preferred embodiment of the present invention, tactile sensor 13 includes a plurality of accelerometers to be used as a motion tracking system for determination of probe coordinates relative to the examined prostate. In an alternate preferred embodiment of the present invention, tactile sensor 13 comprises a magnetometer based orientation tracking system system. Thereafter, pressure response data is used in real time to generate mechanical imaging results, as described in more detail below.

Alternatively, probe 10 can be applied against or adjacent to any gland or tissue such as by being applied through a natural opening of a subject or against a gland or tissue of a subject. Probe 10 can also be used during or after drug delivery and other types of treatments.

Figure 2:
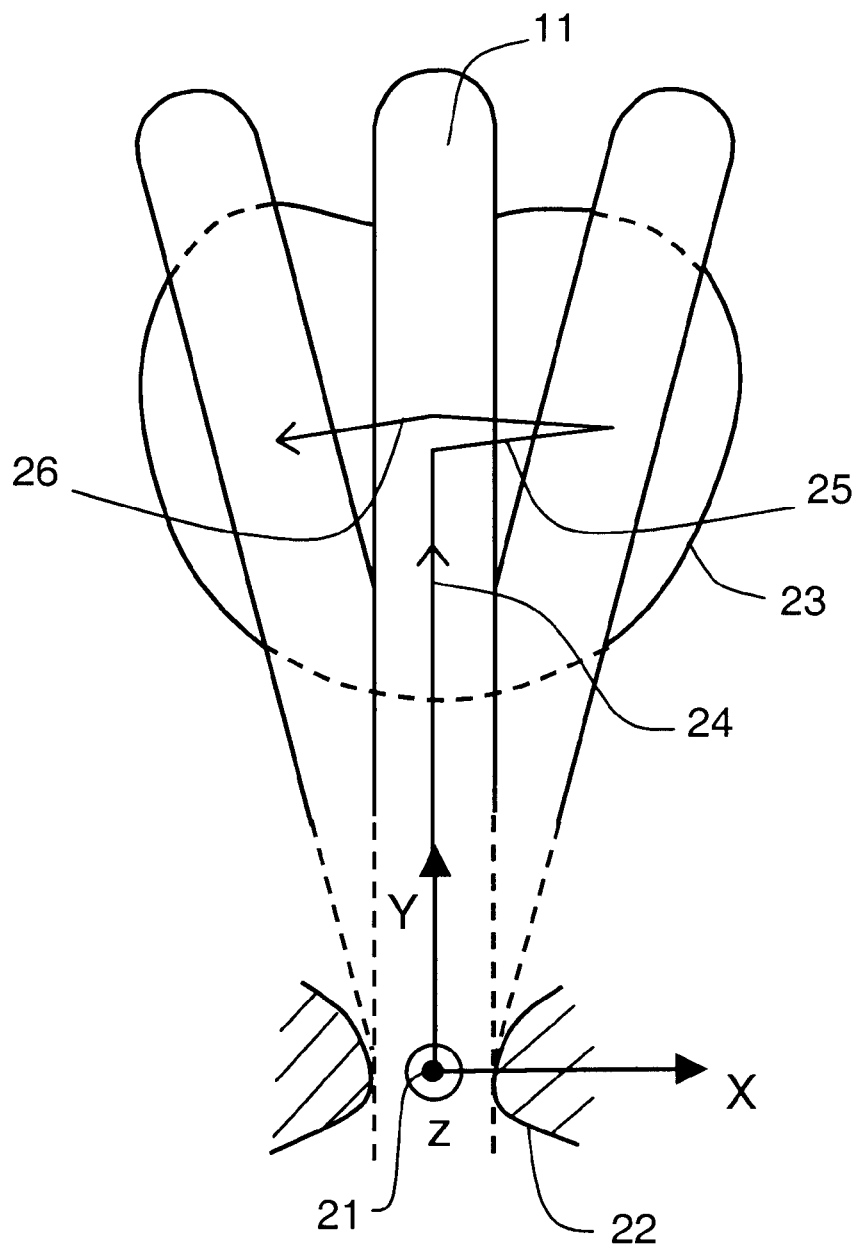
FIG. 2 is a schematic diagram illustrating the relative position of a head with a tactile sensor during prostate examination.

FIG. 2 is a schematic diagram illustrating the relative position of head 11 with tactile sensor 13 during prostate examination while periodically pressing probe 10 against prostate 23 in accordance with an embodiment of the method of the present invention. First, head 11 of probe 10 is inserted into the rectum along axis Y to a predetermined depth without pressing against prostate 23 in order to minimize displacement of the prostate. Second, head 11 is pressed against prostate 23 at a site positioned on trajectory 24 to receive a real time cross-sectional view along axis Y of prostate 23 on display 15. Preferably, tactile sensor 13 has a linear dimension greater than the axial length of prostate 23. In the preferred embodiment tactile sensor 13 has a linear dimension exceeding the axial length of an average prostate, which typically varies between about 25 to about 45 mm. Accordingly, it is possible to observe the pressure pattern produced by entire prostate after a single compression. Third, head 11 having tactile sensor 13 contacting prostate 23 is moved along axis Y to adjust the location of prostate 23 close to the center of tactile sensor 13. Fourth, head 11 is moved along trajectory 25, 26 to laterally pass from one side of prostate 23 to the other while pressing against prostate 23 at a plurality of sites along trajectory 26. Periodic pressing along trajectory 26 provides prostate geometrical features along axis X. Another procedure such as oscillation of head 11 radially from sphincter 22 with simultaneous pressing against prostate 23 can be added to increase linear resolution of mechanical imaging along axis Y.

Figure 3:
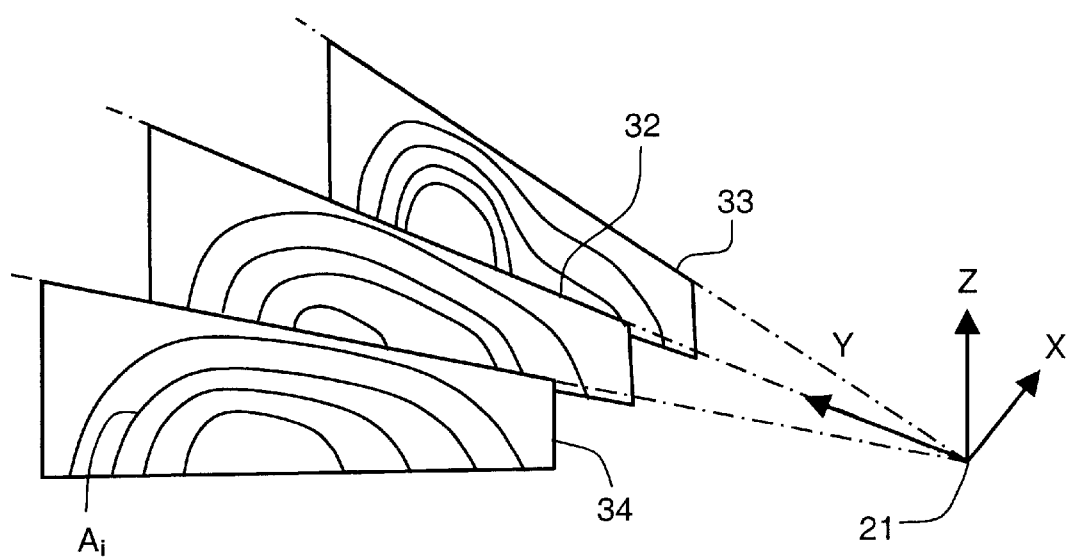
FIG. 3 is a perspective view of real time pressure profiles which characterize cross-sections of the examined prostate obtained by pressing the probe against the prostate at the regions shown in FIG. 2.

Referring to FIG. 3, perspective views of real time pressure profiles which characterize cross-sections 32, 33 and 34 of the examined prostate obtained as the result of pressing the probe against the prostate are shown in coordinate system 21 with the origin placed at the sphincter 22, as shown in FIG. 2. All pressings against the prostate are represented in a vertical direction along axis Z. Cross-sections 32, 33 and 34 are calculated in real time for each pressing against the prostate and are represented on the display by lines of equal pressure $A_i$ in accordance with the procedure described below.

Figure 4:
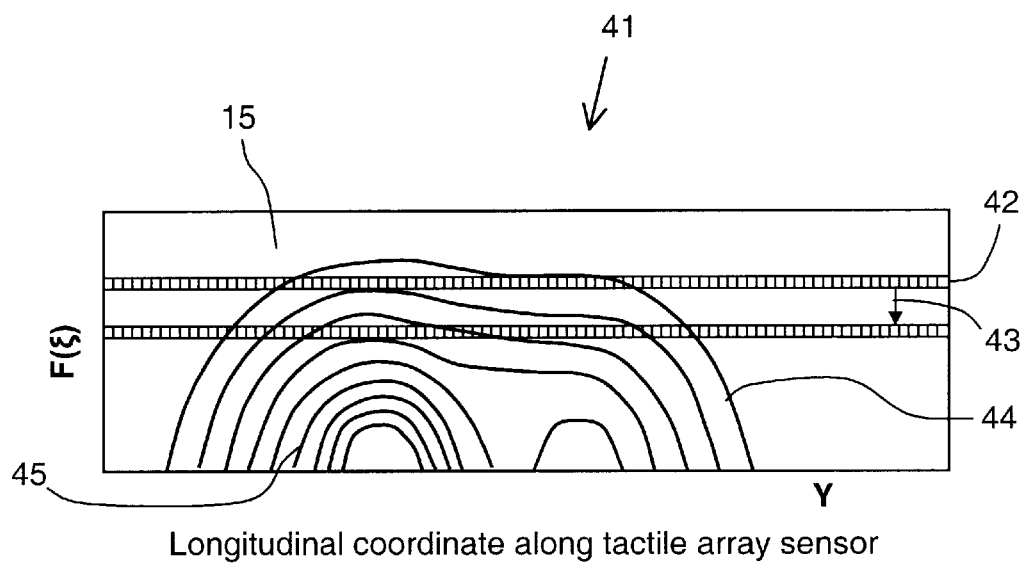
FIG. 4 is an illustration of a topographic picture for characterizing method of real time synthesizing a two-dimensional prostate image for the prostate device in accordance with an embodiment of the method of the present invention.
Figure 5A:
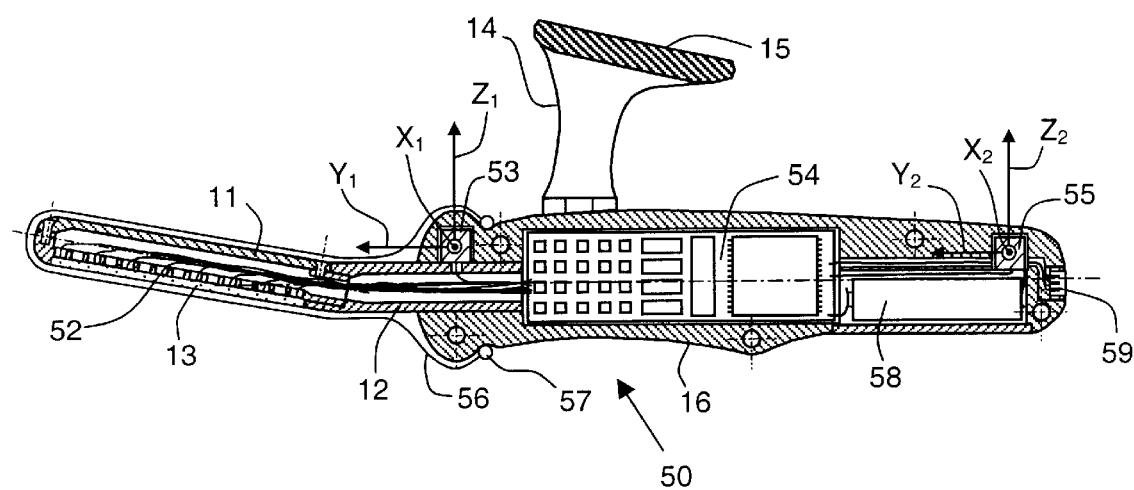
FIG. 5A is a cross-sectional side view of the probe including a tactile sensor with accelerometer based motion tracking system, and electronic unit with a two-dimensional display attached to the probe handle in accordance with a preferred embodiment of the device of the present invention.
Figure 5B:
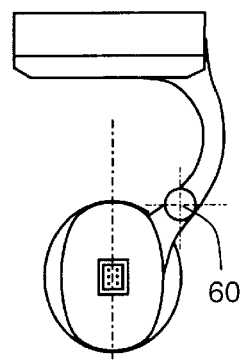
FIG. 5B is a rear view of the probe shown in FIG. 5A.

FIG. 4 illustrates a topographic picture for characterizing an embodiment of a method of real time synthesizing two-dimensional prostate image during pressing the probe against the prostate. It is advantageous to use a color scale for representation of the different pressure levels at pressure transducers of tactile sensor 13 for improved differentiation between pressure levels. The momentary pressure response data can be visualized as color coded line 42. The location of line 42 on topographic picture 41 with coordinates Y and F(ξ) represents the tactile sensor position relative to the examined prostate. Tactile sensor position and pressure on pressure transducers are changing as the head of the probe is pressed against the prostate. Correspondingly, line 42 is shifted along coordinate F(ξ) on display 15 as shown by arrow 43 leaving a colored trace of the previous location of line 42 behind. Each line drawn on display 15 gradually disappears losing its brightness and contrast within a time constant of about 1 second for improved visual perception of the different locations of line 42.

Coordinate Y on display 15 is the longitudinal coordinate along tactile sensor 13, as shown in FIG. 4. Different parameters can be used as the F(ξ) coordinate. In preferred embodiment of the method, the coordinate F(ξ) is an average pressure from all pressure transducers or a portion of transducers of tactile sensor 13. In another preferred embodiment of the method, the coordinate F(ξ) is spatial coordinate Z (see FIG. 3). In yet another embodiment of the method, coordinate F(ξ) is the running time. Lines 44 of equal pressure can be drawn on two-dimensional color display 15. Preferably, lines 44 have a predetermined color to represent the prostate shape and lines 45 corresponding to a higher pressure have a predetermined second color to represent color regions with increased hardness inside the prostate. Pressure gradient analysis of pressure data can be used to determine the prostate shape and its inner structure.

FIGS. 5A and 5B and FIGS. 6A and 6B illustrate in more detail a preferred embodiment of device 10 shown in FIG. 1 with tactile sensor 13 having an accelerometer based motion tracking system 50. Accelerometer based motion tracking system 50 comprises at least two three-axis accelerometers 53, 55 which can be used to distinguish the gravity and inertia signal components. Preferably, accelerometer 53 can be located in handle 16 close to head 11, so that during prostate examination accelerometer 53 is located near the sphincter and is more sensitive to angle orientation of probe 10 than to linear accelerations. Accelerometer 55 preferably is located in handle 16 at a maximum distance from head 11 so that during prostate examination accelerometer 55 is more sensitive to angular acceleration of probe 10 than to linear acceleration. Additional accelerometers can be incorporated into shaft 12 or head 11.

Tactile sensor 13 of the device for real time mechanical imaging of the prostate is incorporated into head 11. Tactile sensor 13 comprises pressure transducer array 52. Pressure transducer array 52 preferably comprises a plurality of piezopolymer transducers, or micro-machined piezoresistive transducers, or capacitive pressure transducers covered by an elastic compound.

Cover 56 covers head 11 and shaft 12. Preferably, cover 56 is flexible. Cover 56 is held by fixing ring 57 to handle 16. Cover 56 can be removed from probe 10 after use and discarded before the next use. Thereafter, a new cover 56 can be placed over head 11 and shaft 12 before the next use for providing improved hygienics of the prostate examination. For example, cover 56 can be formed of thin elastic material such as latex.

Figure 6A:
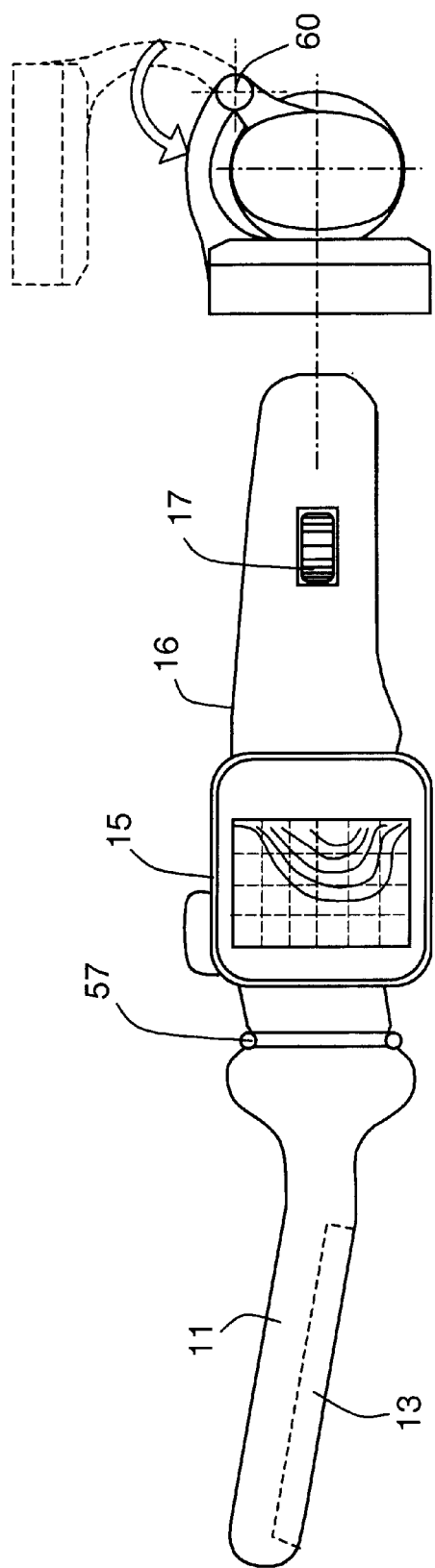
FIG. 6A is a side and rear view of the probe with a two-dimensional display folded into the review position.
Figure 6B:
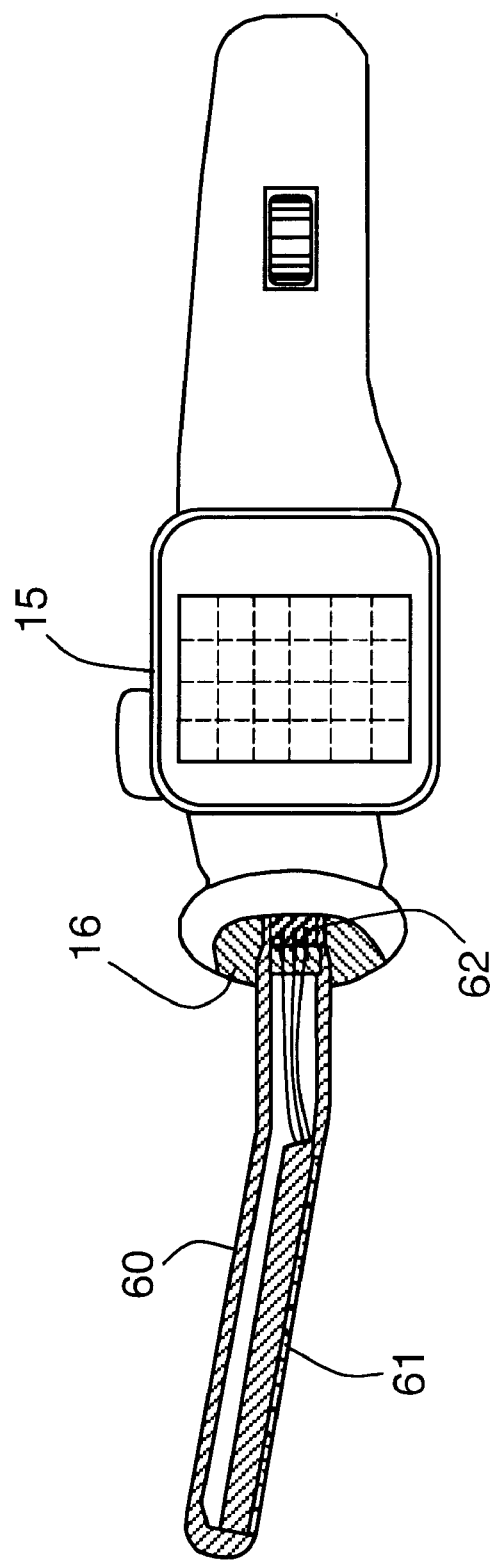
FIG. 6B is a cross-sectional side view of the probe head including disposable pressure sensor head.

In the preferred embodiment, tactile sensor 13 has a linear dimension exceeding the axial length of an average prostate, which typically varies between about 25 to about 45 mm. In another preferred embodiment, pressure sensing head 60 includes pressure transducers 61 removably connected to handle 16 by electrical and mechanical connector 62, as shown in FIG. 6B. Pressure sensing head 60 including pressure transducers 61 can be disposable.

Figure 6C:
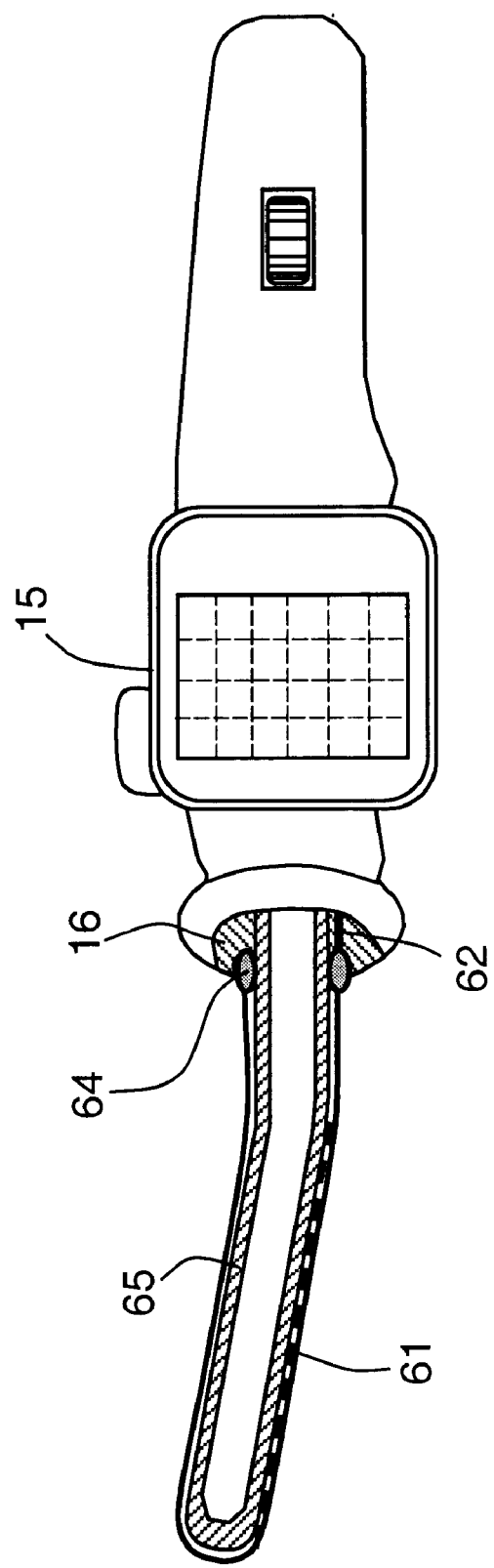
FIG. 6C is a cross-sectional view of the probe including a disposable pressure transducers.

In another preferred embodiment, probe head 65 unremovably connected to handle 16, and pressure sensitive transducers 61 can be removable attached to handle 16 by electrical and mechanical connector 62 and lock 64, as shown in FIG. 6C. In this embodiment, pressure sensitive transducers 61 can be disposable.

Electronic unit 54, power source 58 and computer port 59 preferably can be fitted in handle 16. Electronic unit 54 is coupled to tactile sensor 13 and accelerometer 53, 55. Power source 58 is coupled to electronic unit 54. Control wheel 17 mounted on handle 16 can be used for producing "start" and "stop" signals during the prostate examination procedure, and for operating in review mode, as shown in FIG. 6A. In the review mode, the physician may examine on display 15 stored data received from different patients or transfer data to an external computer. Display 15 is connected to handle 16 through display support 14 equipped with hinge 60 to fix display 15 at two positions: an examination mode as shown in FIG. 5 and a review mode as shown in FIG. 6A. In the examination mode, display 15 shows a real time pressure profile, which characterizes cross-section of examined prostate during pressing against the prostate with visualization of the prostate inner structure and prostate geometrical parameters.

Figure 7A:
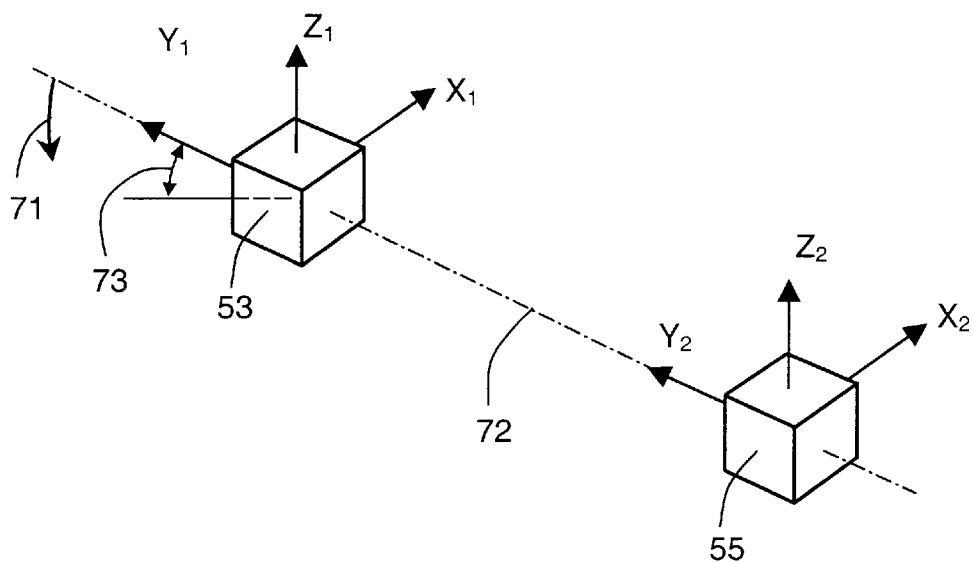
FIG. 7A is a schematic diagram of an accelerometer based motion tracking system in accordance with an embodiment of the device of the present invention.

Referring to FIG. 7A a diagram of accelerometer based motion tracking system 50 is shown in accordance with a preferred embodiment of the method of the present invention. Accelerometer based motion tracking system 50 includes at least two three-axis accelerometers 53, 55, which generate analog signals while moving the probe during prostate examination. As far as the distance 72 and relative orientation of accelerometers 53 and 55 are known, a three-dimensional trajectory can be evaluated by double integration of all analog signals received from accelerometers 53, 55 and by restoration of probe head trajectory relative to a fixed point.

Additionally, an improved precision trajectory can be determined by the following consideration. Since three-axis accelerometer 53 is located near the sphincter during the pressing against the prostate as shown by arrow 71, accelerometer 53 with sensitivity axis along $Y_1$ can be used as a tilt sensor to determine elevation data 73 of the probe. Synchronous data analysis from accelerometers 53, 55 with sensitivity axes $Y_1$ and $Y_2$ allows one to exclude the influence of angular acceleration on elevation data 73. The vertical movement of the probe can be determined by double integration of signals from $Z_1$ of accelerometer 53 and $Z_2$ of accelerometer 55 taking into account changing in elevation of the probe. For more precise determination of coordinate Z to visualize prostate cross-section (as shown in FIG. 4), the rotation data relative to axis 72 from tilt $X_1$ of accelerometer 53 and $X_2$ of accelerometer 55 can be added. To determinate the lateral displacement of the probe from one site of pressing against the prostate to another along coordinate X (see FIG. 2), the differential signal from accelerometers $X_1$ and $X_2$ are double integrated taking into account possible changing in rotation and elevation of the probe. It is useful to consider a point with maximum pressure on tactile sensor during pressing against the prostate as a starting spatial point with zero motion acceleration to calculate the trajectory of the probe relative to the point with maximum pressure in the tactile sensor.

Figure 7B:
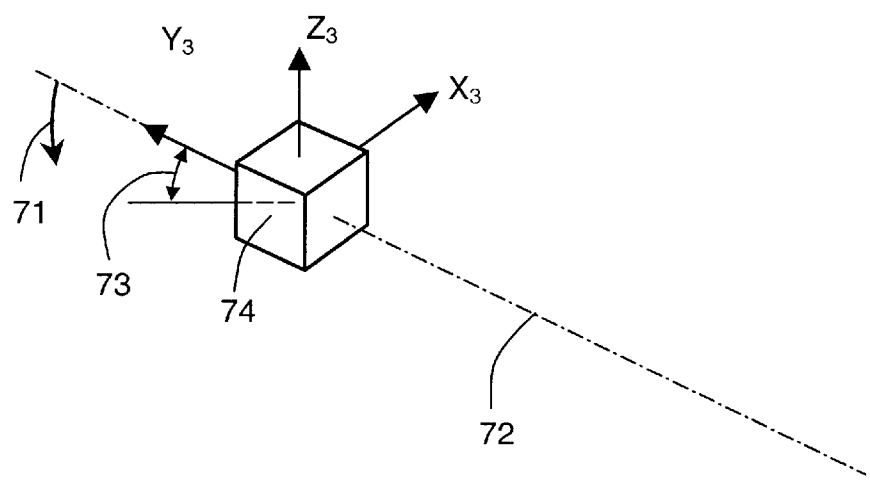
FIG. 7B is a schematic diagram of a magnetometer based motion tracking system in accordance with an embodiment of the device of the present invention.

Referring to FIG. 7B a diagram of magnetometer based orientation tracking system 75 is shown in accordance with a preferred embodiment of the method of the present invention. Magnetometer based orientation tracking system 75 includes at least one triaxial magnetometer 74 which generates analog signals by changing the probe orientation relative to the Earth's magnetic field while moving the prove during prostate examination. As far as the probe orientation is known, a relative site of the pressing of the prostate can be determined. Alternatively, a motion tracking system can be based on a combination of accelerometers and magnetometers or a combination of gyroscopes and accelerometers.

Figure 8:
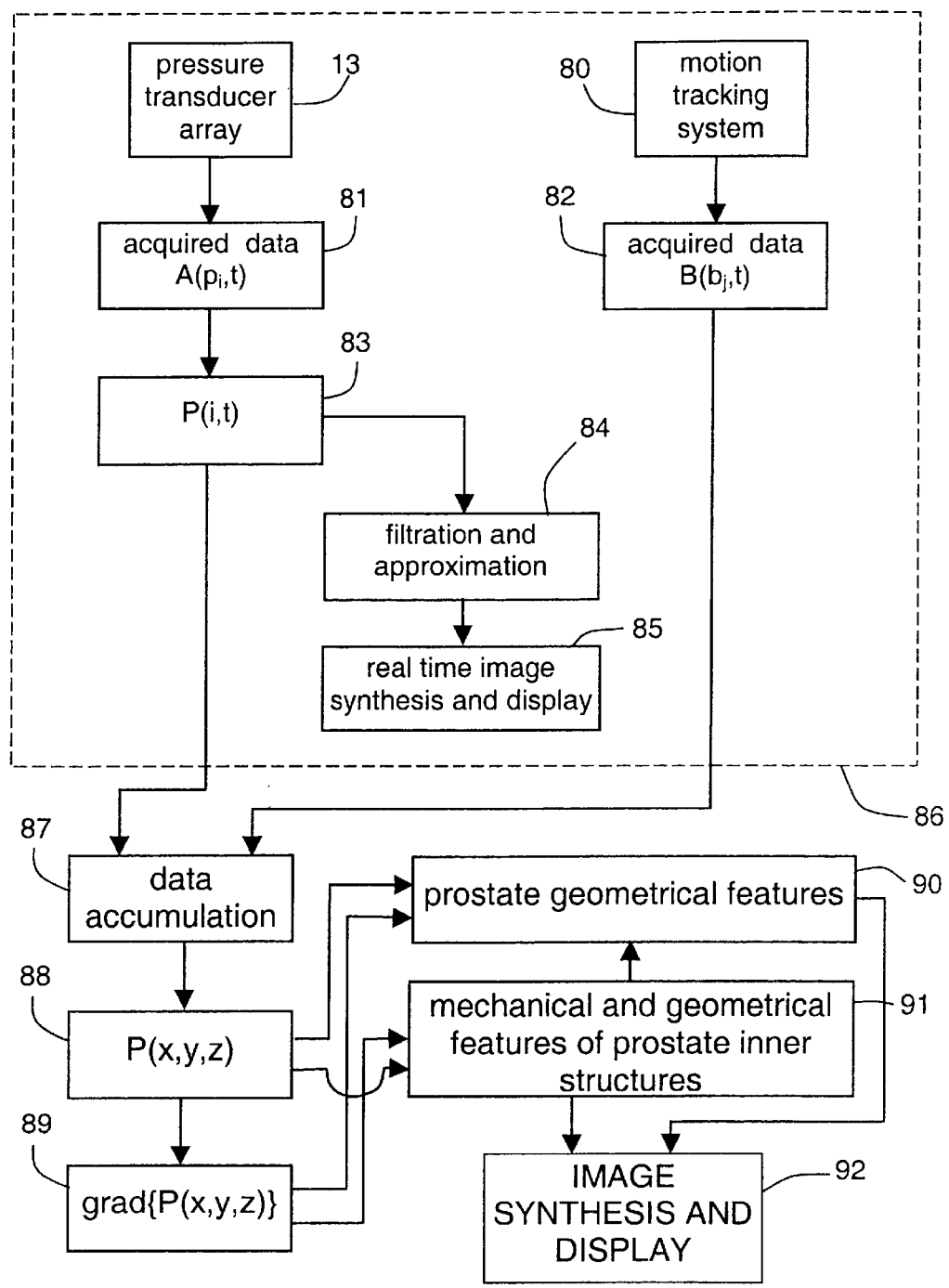
FIG. 8 shows a flow chart describing steps for obtaining diagnostic information in accordance with an embodiment of the method of the present invention.

FIG. 8 is a flow chart of the preferred method of calculating two-dimensional and three-dimensional prostate images. Pressure data from pressure transducer array of tactile sensor 13 and position data from motion tracking system 50 are acquired in real time during prostate examination. Analog signals corresponding to pressures received from all pressure transducers 52 of tactile sensor 13 form pressure data set 81 denoted by $A(p_i,t)$, where $p_i$ is pressure signal for pressure transducer with number i at time t. Analog signals representing accelerations and angular orientation of the probe generated in response to movement of the probe during prostate examination received from motion tracking system 50, form motion data set 82 denoted as $B(b_j,t)$, where $b_j$ is signal corresponding to j accelerometer at time t. Accelerator based motion tracking system 50 can receive responses from accelerometers used as tilt sensors, as described above. In block 83, pressure data set 81 is transformed into absolute pressure data $P(i,t)$, where P is the force imposed on transducer i at time t, calculated in accordance with calibration data of pressure transducers 52. In block 84, data $P(i,t)$ is processed by a conventional approximation method, such as described for example by T. J. Rivlin, *An introduction to the Approximation of Functions*, Dover Publications, Inc., New York (1969), to reduce noise originating from force measurement errors and from artefacts related to prostate movement. In block 85, corrected data $P(i,t)$ is transformed into a displayable format and represented on display 15. All operations in block 86 take place in real time during prostate examination.

Simultaneously, the prostate examination data including said pressure data set $P(i,t)$ and motion data set $B(b_j,t)$ are accumulated in block 87. In block 88, the coordinates of each pressure transducer 52 of tactile sensor 13 are calculated in the coordinate system with the origin at sphincter 22 (see FIG. 2) and the patterns of pressure responses $P(x,y,z)$ of examined prostate are calculated. In block 89, a pattern of pressure gradient responses represented by $\text{grad}\{P(x,y,z)\}$ is calculated from the pattern of pressure responses of the prostate by a conventional method such as described for example by D. Redfern and C. Campbel, *The Matlab 5 Handbook*, Springer-Verlag New York, Inc. (1998). In block 91, mechanical and geometrical features of the prostate inner structures are determined from the pressure gradient responses. In block 90, the pattern of pressure responses of the prostate $P(x,y,z)$ is corrected subject to distortions from the stiffer tissue inside the prostate which are revealed in the pressure gradient responses to determine prostate geometrical features. In block 92, the prostate image is synthesized from data generated in block 91 and data generated in block 90. After having approximated smooth surfaces of equal pressures, it is possible to calculate hardness distribution inside the prostate using the pattern of pressure gradient responses. The surface of the examined prostate can be obtained by calculating the first maximum of the second derivative of $P(x,y,z)$ along normal to prostate surface by an iteration algorithm.

The synthesized image can be displayed on a two-dimensional or linear display coupled to handle 16. An average level of pressure applied to tactile sensor 13, the position, real trajectory of pressure transducers and the predetermined pattern of trajectories for movement of the probe can be indicated in real time in a plane projection over the prostate image on the same display.

Figure 9:
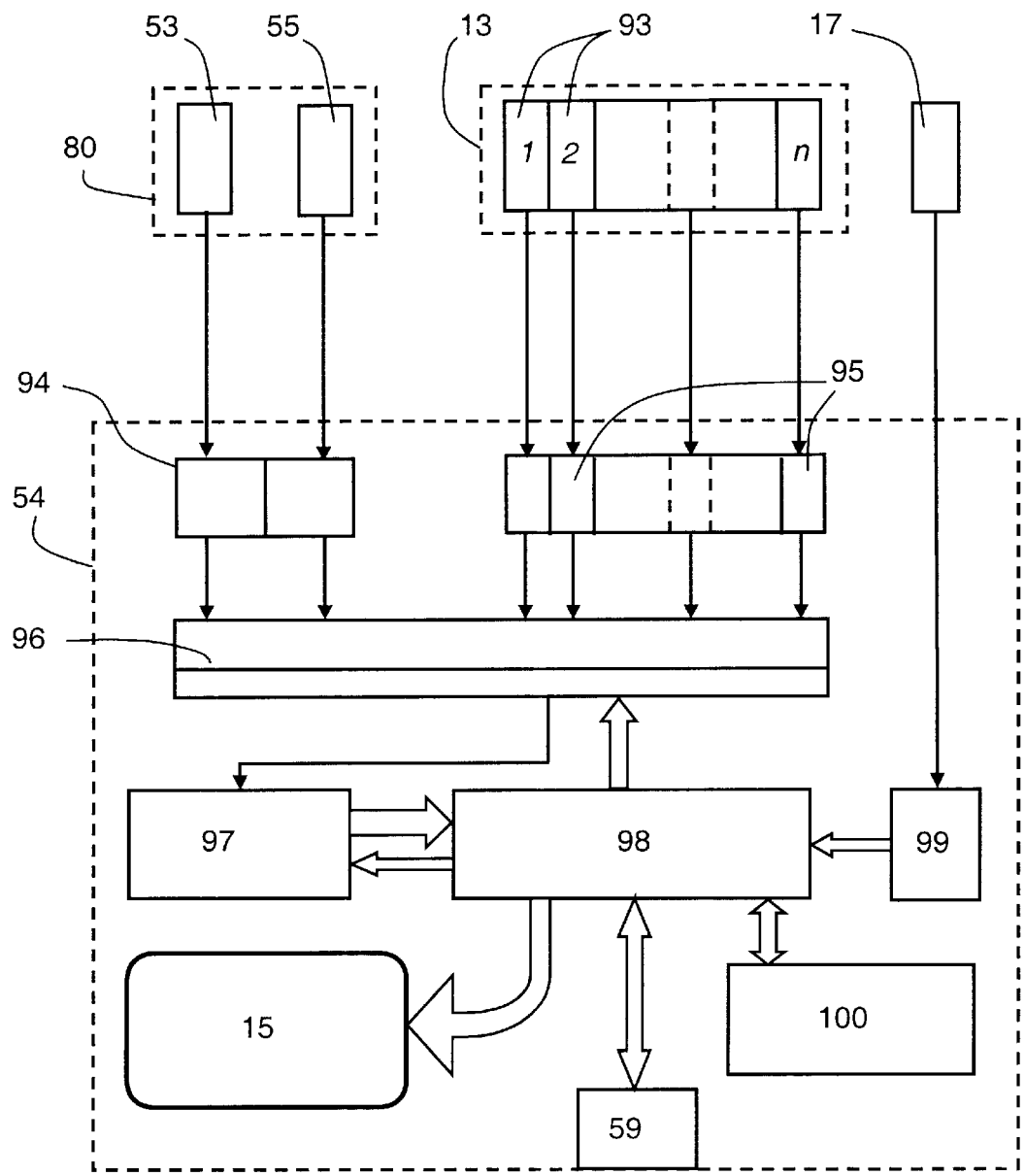
FIG. 9 is a schematic diagram illustrating the functional structure of the system in accordance with an embodiment of the device of the present invention.

FIG. 9 is a schematic diagram of a preferred embodiment of electronic unit 54 mounted in handle 16 of probe 10 shown in FIG. 5. A plurality of pressure transducer elements 93 forms tactile sensor 13. Pressure sensing circuit 95 is formed of a plurality of amplifiers, converters and integrators to amplify and convert respective signals generated by pressure transducer elements 93 for detecting the force imposed on each pressure transducer element 93 of tactile sensor 13 during prostate examination. A plurality of amplifiers 94 amplify signals generated by respective accelerometers 53, 54 of accelerator motion tracking system 50, for detecting the position of the probe during pressing against the prostate and movement of the probe from one pressing site to another. The amplified signals from amplifiers 94 and 95 are applied to multiplexer 96. Multiplexed signals are converted to digital signals by analog-to-digital converter 97 and fed to processor 98. Processor 98 is used for signal processing to calculate the position of each pressure transducer elements 93 during prostate examination, to approximate and correct mechanical images of the prostate and surrounding tissues, for separation and analysis of the prostate mechanical images, for determining the prostate geometrical features and mechanical features of prostate inner structures such as lesions, nodules, stiffer tissue and the like, and for prostate image synthesis, as described in the method illustrated in FIGS. 3, 4 and 8.

Display 15, including a display screen and a controller, is connected to processor 98, thereby displaying the real time prostate image, prostate examination process and the final results of the examination. Control wheel 17 is connected to processor 98 through driver 99 for controlling the prostate examination process, data analysis and data review. Processor 98 communicates with analog-to-digital converter 97 and multiplexer 96 for sending data and control signals. Storage unit 100 can be used in electronic unit 54 for storing the results of the prostate examination generated by processor 98 having computer port 59 to transfer the stored data to an external computer.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A method for real time mechanical imaging the prostate comprising the steps of:
   inserting a transrectal probe into a rectum to a predetermined depth, said transrectal probe having a tactile sensor with a linear dimension exceeding an axial length of an average prostate in the range of about 25 mm to about 45 mm;
   acquiring pressure response data and motion data from said tactile sensor during movement of said tactile sensor along predetermined trajectories overlaying said prostate;

real time calculating and displaying of one or more pressure profiles which characterize a cross-section of said prostate;

calculating a pattern of pressure gradient responses from said pressure response data and motion data;

synthesizing a mechanical image of the prostate and its inner structure from said pressure gradient responses; and displaying said one or more pressure profiles and said mechanical image.

2. The method of claim 1 wherein said tactile sensor comprises a tactile sensor array and said movement of said tactile sensor along each of said trajectories is performed with periodic pressing of said tactile sensor array against the prostate.

3. The method of claim 2 wherein before said pressing of said tactile sensor against the prostate further comprising the step of:

adjusting of an initial pressing site to locate the prostate under a center of said tactile sensor.

4. The method of claim 1 wherein said predetermined trajectories are formed of at least one radial trajectory passing through the sphincter along the axis of rectum and at least one lateral trajectory passing from one side of the prostate to the other.

5. The method of claim 2 wherein said periodic pressing is accompanied with oscillating said tactile sensor along the probe axis.

6. The method of claim 1 wherein said pressure profiles are displayed in real time as a function of the deformation of prostate produced by said tactile sensor pressed against the prostate.

7. The method of claim 1 wherein said pressure profiles are displayed as a function of the force applied to said tactile sensor while pressing against the prostate.

8. The method of claim 1 wherein said motion data is obtained from an accelerometer based motion tracking system and position of said tactile sensor relative to the prostate is calculated by the step of integrating linear and angular accelerations.

9. The method of claim 1 wherein said motion data is obtained from a magnetometer based motion tracking system.

10. The method of claim 1 wherein said pressure profiles are displayed as a plurality of color coded lines which gradually disappear losing their brightness and contrast.

11. The method of claim 10 wherein said color coded lines disappear with a time constant of about 1 second.

12. A device for real time mechanical imaging of the prostate comprising:

a probe sized to fit within the rectum and having a head with tactile sensor connected by a shaft to a handle, said tactile sensor having a linear dimension exceeding an axial length of an average prostate in the range of about 25 mm to about 45 mm;

an electronic unit receiving pressure response data and motion data from said tactile sensor;

means for real time calculating pressure profiles which characterize cross-section of the prostate from said pressure response data and motion data;

means for calculating mechanical images of the prostate from said pressure response data and motion data;

a display coupled to said handle for displaying said pressure profiles and said mechanical images of the prostate and its inner structure; and a control wheel mounted on said handle, said control wheel operating to control said electronic unit.

13. The device of claim 12 wherein said tactile sensor comprises a pressure transducer array and a motion tracking system.

14. The device of claim 13 wherein each pressure transducer in said pressure transducer array is a micro-machined piezoresistive transducer.

15. The device of claim 13 wherein each pressure transducer in said pressure transducer array is a piezopolymer transducer.

16. The device of claim 13 wherein each pressure transducer in said pressure transducer array is a capacitive transducer.

17. The device of claim 13 wherein said motion tracking system comprises a plurality of accelerometers.

18. The device of claim 17 wherein at least two of said plurality of accelerometers have sensitivity axes directed along the axis of the probe to separate gravity and inertial signal components during pressing said tactile sensor against the prostate.

19. The device of claim 18 wherein one of said accelerometers directed along the axis of the probe is located on said shaft at a first end of said handle which is connected to said shaft and is adjacent to the sphincter when said probe is fit within the rectum and a second one of said accelerometers directed along the axis of the probe is located at a second end of said handle.

20. The device of claim 17 wherein at least two of said accelerometers are used as tilt sensors to determinate rotation and elevation angles of said probe during prostate examination.

21. The device of claim 17 wherein at least two of said accelerometers are used to determinate azimuth angular acceleration of said probe during prostate examination.

22. The device of claim 12 wherein said motion tracking system comprises a plurality of magnetometers to determinate probe position during prostate examination.

23. The device of claim 12 wherein said display is connected to said handle through a support equipped with a hinge to fix said display in a first position of an examination mode and a second position of a review mode.

24. The device of claim 12 further comprising a flexible cover which covers said head and said shaft and fixing for attaching said flexible cover to said handle.

25. The device of claim 24 wherein said flexible cover is disposable.

26. The device of claim 12 wherein said tactile sensor comprises pressure transducers made in the form of a sheath covering said head and connected to said shaft by an electrical connector.

27. The device of claim 26 wherein said sheath with pressure transducers is disposable.

28. The device of claim 12 wherein said shaft with said pressure sensing head is removably attached to the handle by an electrical connector.

29. The device of claim 28 wherein said shaft with said pressure sensing head are disposable.

30. A method for real time mechanical imaging tissues or glands comprising the steps of:

applying a probe to said tissues or glands or adjacent to said tissues or glands;

acquiring pressure response data and motion data from said tactile sensor during movement of said tactile sensor along predetermined trajectories;

real time calculating and displaying of one or more pressure profiles which characterize a cross-section of said tissues or glands;

real time calculating a pattern of pressure gradient responses from said pressure response data and motion data;

real time synthesizing a mechanical image of said tissues or glands and its inner structure from said pressure gradient responses; and real time displaying of said one or more pressure profiles and said mechanical image during examination of said tissue or gland.

31. The method of claim 30 wherein said method is applied during or after drug treatment of said tissue or gland.

32. A system for real time mechanical imaging tissues or glands comprising the steps of:

means for applying a probe to said tissues or glands or adjacent to said tissues or glands;

means for acquiring pressure response data and motion data from said tactile sensor during movement of said tactile sensor along predetermined trajectories;

means for real time calculating and displaying of one or more pressure profiles which characterize a cross-section of said tissues or glands;

means for calculating a pattern of pressure gradient responses from said pressure response data and motion data;

means for synthesizing a mechanical image of said tissues or glands and its inner structure from said pressure gradient responses; and means for displaying said one or more pressure profiles and said mechanical image during examination of said tissue or gland.

33. The system of claim 32 wherein said probe is applied during or after drug treatment of said tissue or gland.

* * * * *